United States Patent
Van Der Schaaf et al.

(10) Patent No.: US 7,777,049 B2
(45) Date of Patent: Aug. 17, 2010

(54) CRYSTALLINE FORMS OF RIZATRIPTAN BENZOATE

(75) Inventors: Paul Adriaan Van Der Schaaf, Hagenthal-le-Haut (FR); Jörg Berghausen, Lörrach (DE); Fritz Blatter, Reinach (CH); Martin Szelagiewicz, Münchenstein (CH); Ulrich Berens, Binzen (DE)

(73) Assignee: ratiopharm GmbH, Ulm (DE)

( * ) Notice: Subject to any disclaimer, the term of this patent is extended or adjusted under 35 U.S.C. 154(b) by 670 days.

(21) Appl. No.: 10/585,448

(22) PCT Filed: Jan. 5, 2005

(86) PCT No.: PCT/EP2005/000034

§ 371 (c)(1),
(2), (4) Date: Nov. 28, 2006

(87) PCT Pub. No.: WO2005/068453

PCT Pub. Date: Jul. 28, 2005

(65) Prior Publication Data

US 2008/0249149 A1    Oct. 9, 2008

Related U.S. Application Data

(60) Provisional application No. 60/535,674, filed on Jan. 9, 2004.

(30) Foreign Application Priority Data

Jan. 9, 2004 (EP) .................................. 04100053

(51) Int. Cl.
*C07D 401/12* (2006.01)
(52) U.S. Cl. .................................................. 548/266.4
(58) Field of Classification Search ............. 548/266.4; 514/383
See application file for complete search history.

(56) References Cited

U.S. PATENT DOCUMENTS 5,567,824 A    10/1996    Chen et al.

FOREIGN PATENT DOCUMENTS

EP    0 497 512 A2    8/1992
GB    2315673    2/1998

OTHER PUBLICATIONS

A. Maureen Rouhi, Chemical & Engineering News, Feb. 24, 2003, pp. 32-35.*
Haleblian et al. Journal of Pharmaceutical Sciences, Aug. 1969, vol. 58, No. 8, pp. 911-929.*
Written Opinion of the International Searching Authority issued in PCT/EP05/000034 (2005).

* cited by examiner

*Primary Examiner*—Rebecca L Anderson
*Assistant Examiner*—Shawquia Young
(74) *Attorney, Agent, or Firm*—Chalin A. Smith; Smith Patent Consulting, LLC

(57) ABSTRACT

The present invention is directed to the novel polymorphic Form A and Form B of Rizatriptan benzoate, processes for the preparation thereof and pharmaceutical compositions comprising these crystalline forms.

14 Claims, 2 Drawing Sheets

CRYSTALLINE FORMS OF RIZATRIPTAN BENZOATE

This application is a Rule 371 U.S. National Phase Filing of PCT/EP05/000034, filed Jan. 5, 2005, which, in turn, claims priority to European Patent Application No. 04.100053.0, filed Jan. 9, 2004 and U.S. Provisional Patent Application Ser. No. 60/535,674, filed Jan. 9, 2004, the contents of which are incorporated by reference herein in their entirety.

The present invention is directed to crystalline forms of Rizatriptan benzoate, processes for the preparation thereof and pharmaceutical compositions comprising these crystalline forms.

The present invention relates to novel crystalline forms of Rizatriptan benzoate. Rizatriptan benzoate is known by the chemical name, N,N-dimethyl-5-(1H-1,2,4-triazol-1-ylmethyl)-1H-indole-3-ethanamine benzoate. Rizatriptan has the following formula:

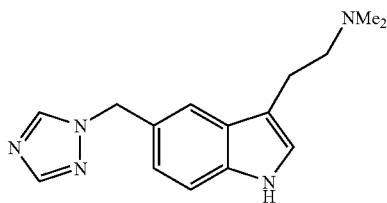

Rizatriptan benzoate is a selective 5-hydroxytryptamine$_{1B/1D}$ (5-HT$_{1B/1D}$) receptor agonist, and is marketed as an oral formulation for acute treatment of migraine.

Processes for the preparation of Rizatriptan benzoate are disclosed in the patents GB-A-2315673, WO-A-95/32197, EP-A-497512, and in the publications by Cheng-yi Chen et al. in Tetrahedron Letters (1994), vol. 35, pages 6981-6984 and L. J. Street et al. in Journal of Medicinal Chemistry (1995), vol. 38, pages 1799-1810. In the processes described in the above mentioned patents and publications Rizatriptan benzoate is isolated from ethanol as a white solid with a melting point of 178-180° C. However, there is still a need to produce Rizatriptan benzoate in a reproducible, pure and crystalline form to enable formulations to meet exacting pharmaceutical requirements and specifications. Furthermore, it is known that pharmaceutical substances can exhibit polymorphism. Polymorphism is commonly defined as the ability of any substance to have two or more different crystal structures. Drug substances may also encapsulate solvent molecules when crystallized. These solvates or hydrates are referred to as pseudopolymorphs. It is also possible that the amorphous form is encountered. Different polymorphs, pseudopolymorphs or the amorphous form differ in their physical properties such as melting point, solubility etc. These can appreciably influence pharmaceutical properties such as dissolution rate and bioavailability. It is also economically desirable that the product is stable for extended periods of time without the need for specialized storage conditions. It is therefore important to evaluate polymorphism of drug substances. In addition, the discovery of new crystalline polymorphic forms of a drug enlarges the repertoire of materials that a formulation scientist has with which to design a pharmaceutical dosage form of a drug with a targeted release profile or other desired characteristics.

It has now surprisingly been found that Rizatriptan benzoate exhibits polymorphism and can be obtained from certain solvents under certain crystallisation conditions in a very stable, well-defined crystalline form, herein designated as Form A, whereas under certain other crystallisation conditions a meta-stable crystalline form, herein designated as Form B, can be obtained.

Accordingly, the present invention is directed to the polymorphic Forms A and B of Rizatriptan benzoate.

One object of the invention is a crystalline polymorph of N,N-dimethyl-5-(1H-1,2,4-triazol-1-ylmethyl)-1H-indole-3-ethanamine benzoate, herein designated as Form A, which exhibits a characteristic X-ray powder diffraction pattern with characteristic peaks expressed in d-values (Å) and in 2θ as given in Table 1 (vs=very strong intensity, s=strong intensity, m=medium intensity, w=weak intensity, vw=very weak intensity).

TABLE 1 d-spacings and 2θ angles for Form A.

| Angle °2θ | d-spacing (Å) | Qualitative Relative Intensity |
|---|---|---|
| 8.3 | 10.7 | w |
| 9.2 | 9.6 | w |
| 11.6 | 7.6 | w |
| 12.9 | 6.9 | w |
| 13.6 | 6.5 | vw |
| 14.5 | 6.1 | vw |
| 15.9 | 5.56 | m |
| 16.2 | 5.47 | vw |
| 16.5 | 5.36 | w |
| 17.1 | 5.19 | s |
| 17.7 | 5.00 | m |
| 17.9 | 4.95 | m |
| 18.4 | 4.81 | w |
| 18.9 | 4.70 | vs |
| 19.3 | 4.59 | w |
| 20.3 | 4.38 | vw |
| 21.1 | 4.22 | s |
| 22.2 | 4.00 | s |
| 22.8 | 3.91 | w |
| 23.4 | 3.81 | w |
| 23.9 | 3.72 | w |
| 24.2 | 3.68 | vw |
| 25.0 | 3.56 | s |
| 26.2 | 3.40 | m |
| 27.2 | 3.27 | vw |
| 28.2 | 3.16 | vw |
| 28.9 | 3.09 | w |
| 29.3 | 3.05 | vw |
| 31.1 | 2.87 | vw |
| 31.7 | 2.83 | w |
| 32.0 | 2.79 | vw |
| 33.4 | 2.68 | vw |
| 34.1 | 2.63 | vw |
| 34.7 | 2.59 | vw |
| 36.0 | 2.50 | vw |
| 37.1 | 2.42 | vw |
| 37.9 | 2.38 | vw |
| 39.5 | 2.28 | vw |

Form A of N,N-dimethyl-5-(1H-1,2,4-triazol-1-ylmethyl)-1H-indole-3-ethanamine benzoate is characterized by the very strong intensity and strong intensity peaks, preferably by the above peaks and in addition by the medium intensity peaks, more preferably by the very strong intensity, strong intensity, medium intensity and weak intensity peaks and most preferably all peaks listed above.

Another object of the invention is a crystalline polymorph of N,N-dimethyl-5-1H-1,2,4-triazol-1-ylmethyl)-1H-indole-3-ethanamine benzoate, herein designated as Form B, which exhibits a characteristic X-ray powder diffraction pattern with characteristic peaks expressed in d-values (Å) and in 2θ as given in Table 2 (vs very strong intensity, s=strong intensity, m=medium intensity, w=weak intensity, vw=very weak intensity).

TABLE 2 d-spacings and 2θ angles for Form B.

| Angle °2θ | d-spacing (Å) | Qualitative Relative Intensity |
|---|---|---|
| 7.8 | 11.3 | vw |
| 8.5 | 10.4 | vs |
| 8.9 | 9.9 | vw |
| 11.3 | 7.8 | vw |
| 11.6 | 7.6 | vw |
| 13.2 | 6.7 | vw |
| 13.5 | 6.6 | vw |
| 15.0 | 5.89 | m |
| 15.7 | 5.64 | vw |
| 16.3 | 5.45 | s |
| 16.6 | 5.35 | m |
| 17.1 | 5.18 | w |
| 17.5 | 5.07 | vw |
| 17.9 | 4.95 | s |
| 18.9 | 4.71 | s |
| 20.0 | 4.45 | m |
| 20.4 | 4.36 | m |
| 21.0 | 4.23 | w |
| 21.2 | 4.18 | w |
| 22.4 | 3.97 | m |
| 22.7 | 3.92 | m |
| 22.9 | 3.89 | m |
| 23.6 | 3.76 | m |
| 24.0 | 3.70 | m |
| 24.4 | 3.65 | vw |
| 25.5 | 3.50 | w |
| 25.8 | 3.45 | w |
| 26.4 | 3.38 | vw |
| 27.0 | 3.30 | vw |
| 27.8 | 3.21 | vw |
| 28.2 | 3.16 | vw |
| 28.7 | 3.11 | vw |
| 32.9 | 2.72 | w |
| 34.7 | 2.59 | vw |

Form B of N,N-dimethyl-5-(1H-1,2,4-triazol-1-ylmethyl)-1H-indole-3-ethanamine benzoate is characterized by the very strong intensity and strong intensity peaks, preferably by the above peaks and in addition by the medium intensity peaks, more preferably by the very strong intensity, strong intensity, medium intensity and weak intensity peaks and most preferably all peaks listed above.

The polymorphic Form A of Rizatriptan benzoate is especially characterized by an X-ray powder diffraction pattern as depicted in FIG. 1, whereas the polymorphic Form B of Rizatriptan benzoate is especially characterized by an X-ray powder diffraction pattern as depicted in FIG. 2.

Furthermore, the present invention is directed to processes for the preparation of Form A and Form B of Rizatriptan benzoate.

Form A can be generally prepared by crystallization from cooled solutions of Rizatriptan benzoate in an organic solvent, or mixtures of organic solvents, or a mixture of an organic solvent with a non-solvent selected from hydrocarbons and ethers or water. Preferably the organic solvent is an alcohol, e.g. a $C_1$-$C_8$ alcohol, preferably a primary alcohol, like methanol, 1-butanol or 1-octanol, or esters like ethyl acetate, or a ketone solvent, like acetone or methyl isobutyl ketone. Preferred non-solvents are selected from $C_5$-$C_8$ alkanes such as hexane and/or heptane and ethers such as diethylether, ethyl-butyl ether, ethyl-propyl ether, dipropylether, propyl-butyl ether, dibutylether, tetrahydrofuran, dioxan. Advantageous mixtures include those of an acetate with an alkane, e.g. a $C_5$-$C_8$ alkane like hexane or heptane. Preferably these solutions are cooled from temperatures of about 20° C. to 100° C. down to temperatures of about −20° C. to 10° C. Most preferably from temperatures of about 50° C. to 80° C. down to temperatures of about 0° C. to 5° C. It is also possible to cool from temperatures of about 40° C. to 100° C. down to about room temperature (about 25° C.). Form A can also be generally prepared by evaporation of aqueous solutions, or by evaporation of solutions of Rizatriptan benzoate in a mixture of an organic solvent with water. Preferably the organic solvent is an alcohol, like 2-propanol or 1-butanol, and the amount of water is ranging from 1% to 50%, most preferably about 10% to 20%. Form A can also be generally prepared by adding an organic non-solvent to a solution of Rizatriptan benzoate in a mixture of an organic solvent and water. Preferably the organic solvent is an alcohol, like 2-propanol, or a ketone solvent, like acetone, or tetrahydrofuran.

Form B can be generally prepared by fast crystallization, for example by addition of a solution of Rizatriptan benzoate in an alcohol, or mixtures of an alcohol with another organic solvent, to a non-solvent or vice versa. The alcohol solvent is preferably methanol, and can be mixed with other organic solvents like acetates, preferably ethyl acetate. Examples of non-solvents are alkanes, e.g. $C_5$-$C_8$ alkanes, preferably hexane or heptane. The precipitated Rizatriptan benzoate Form B is preferably isolated by filtration and dried in vacuum. Form B can also be generally prepared by evaporation of an alcoholic solution. Preferably the alcohol is 1-butanol or 2-propanol.

The term non-solvent as used herein should be understood to designate liquid organic compounds in which Rizatriptan benzoate is less soluble as in the liquid organic compounds designated "solvents". The terms non-solvent and cosolvent are used interchangeably herein.

In the above mentioned processes small amounts of seeding crystals of the desired crystalline form may be added to the reaction mixture. Preferably small amounts are about 1 to 20 weight %, more preferably about 5 weight %. Seeding crystals may be added before or, where appropriate, after the step initiating the crystallization (e.g. cooling, addition of non-solvent etc. as described above). Addition before initiating the crystallization is of specific technical interest. Whether in a certain process form A or form B is obtained may depend on the seeding crystals employed in this process, as shown in the examples.

Another object of the present invention are pharmaceutical compositions comprising an effective amount of crystalline polymorphic Form A and/or B of Rizatriptan benzoate, hereinbelow referred to as pharmaceutically active ingredient compositions, for example in combination with a pharmaceutically acceptable carrier.

These polymorphic forms may be used as single component or as mixtures with other crystalline forms or the amorphous form.

As to the novel polymorphic forms of Rizatriptan benzoate it is preferred that these contain 25-100% by weight, especially 50-100% by weight, of at least one of the novel forms, based on the total amount of Rizatriptan benzoate. Preferably, such an amount of the novel polymorphic forms of Rizatriptan benzoate is 75-100% by weight, especially 90-100% by weight. Highly preferred is an amount of 95-100% by weight.

Preferably, the polymorphic form A of Rizatriptan benzoate is free of polymorphic Form B of Rizatriptan benzoate, more preferably free of all other polymorphic or amorphous forms of Rizatriptan benzoate. Preferably, the polymorphic form B of Rizatriptan benzoate is free of polymorphic Form A of Rizatriptan benzoate, more preferably free of all other polymorphic or amorphous forms of Rizatriptan benzoate.

The pharmaceutical compositions of the invention frequently comprise for each part by weight of a crystalline polymorphic form A 0.001 to 100 parts, preferably 0.01 to 10 parts, especially 0.05 to 2 parts by weight of a crystalline polymorphic form B. Of course, pharmaceutical compositions which contain pure polymorphic form A and pharmaceutical compositions which contain pure polymorphic form B of Rizatriptan benzoate are also preferred.

The present invention includes a process for the preparation of a pharmaceutical composition, which process comprises addition of an effective amount of the pharmaceutically active ingredient composition to a pharmaceutically acceptable carrier. The present invention further includes a pharmaceutical composition comprising an effective amount of the pharmaceutically active ingredient composition and a pharmaceutically acceptable carrier. The present invention further pertains to the use of this pharmaceutical composition for the manufacturing of a drug intended for the treatment and/or prevention of migraine, or for the manufacturing of a medicament for the treatment and/or prevention of clinical conditions for which a selective antagonist of $5\text{-HT}_{1B/1D}$-like receptors is indicated. Thus, the present invention also includes a method for the treatment and/or prevention of clinical conditions for which a selective antagonist of $5\text{-HT}_{1B/1D}$-like receptors is indicated, comprising administering to a patient in need of such treatment an effective amount of the pharmaceutical composition of the invention. The present invention also includes a method for the treatment and/or prevention of migraine, comprising administering to a patient in need of such treatment an effective amount of the pharmaceutical composition of the invention.

The compositions of the invention include powders, granulates, aggregates and other solid compositions comprising at least one of the novel forms. In addition, the compositions that are contemplated by the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl, cellulose salts and other substituted and unsubstituted celluloses; starch; pregelatinized starch; inorganic diluents like calcium carbonate and calcium diphosphate and other diluents known to the pharmaceutical industry.

Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that also may be present in the solid compositions further include disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of Rizatriptan benzoate whereupon the properties that distinguish the solid forms of Rizatriptan benzoate are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred unit dosages of the pharmaceutical compositions of this invention typically contain from 1 to 50 mg of the novel Rizatriptan benzoate forms or mixtures thereof with each other or other forms of Rizatriptan benzoate. More usually, the combined weight of the Rizatriptan benzoate forms of a unit dosage are from 2.5 mg to 30 mg, for example 5 or 10 mg.

The following Examples illustrate the invention in more detail. Temperatures are given in degrees Celsius. If not stated otherwise, ambient atmosphere or room temperature is in the range 20-25° C. Abbreviations and symbols used in the Examples and elsewhere:

TBME: tert.-butyl-methyl ether

1 Å stands for $10^{-10}$ m.

EXAMPLE 1

Preparation of Form A 47 mg of rizatriptan benzoate are suspended in 35 ml TBME and heated to 60° C., then 0.2 ml methanol are added at 60° C. to increase the solubility. The almost clear solution is filtered through a 0.22 µm Millipore filtration unit. Then the filtrated solution is cooled to room temperature and near room temperature the still clear solution is seeded with 2 mg rizatriptan benzoate Form A. The temperature is further reduced to 5° C., and the obtained suspension is stored at 5° C. for about 24 hours, before the solid is separated by filtration. The obtained white solid contains crystals with a needle shaped crystal habit, yield 22 mg Form A. The obtained crystal Form A is characterized by an X-ray powder diffraction pattern as shown in FIG. 1.

EXAMPLE 2

Preparation of Form A 70 mg of rizatriptan benzoate are dissolved in 10 ml 1-butanol at 60° C. The temperature of the clear solution is reduced to room temperature and seeded with 2 mg rizatriptan benzoate Form A. The obtained suspension is further cooled to 5° C. and stored at this temperature for about 2 hours. The obtained white crystals were separated by filtration, yielding 20 mg Form A in form of white flakes. The obtained crystal Form A is characterized by an X-ray powder diffraction pattern as shown in FIG. 1.

EXAMPLE 3

Preparation of Form A 21 mg rizatriptan benzoate are dissolved in a mixture of 8.5 ml ethyl acetate and 8.5 ml heptane at 70° C. The clear solution is cooled to room temperature and seeded with 1 mg rizatriptan benzoate Form A. After about 30 minutes storage at 5° C., needle-like crystals start to grow, and the suspension is filtered after 18 hours, yielding 12 mg Form A. The obtained crystal Form A is characterized by an X-ray powder diffraction pattern as shown in FIG. 1.

EXAMPLE 4

Preparation of Form A 24 mg rizatriptan benzoate are dissolved in 3 ml 1-octanol at 70° C. and the obtained solution is cooled to room temperature. About 40 minutes after seeding with 1 mg rizatriptan benzoate Form A the solution becomes turbid due to the progress of the crystallization process. After 20 hours of further phase equilibration, the suspension is filtered, and about 10 mg of Form A as a white powder is obtained after filtration and drying. The obtained crystal Form A is characterized by an X-ray powder diffraction pattern as shown in FIG. 1.

EXAMPLE 5

Preparation of Form A

An aqueous solution of rizatriptan benzoate (10 mg/ml) was evaporated on a watch glass at ambient atmosphere (room temperature), yielding Form A quantitatively. The obtained crystal Form A is characterized by an X-ray powder diffraction pattern as shown in FIG. 1.

EXAMPLE 6

Preparation of Form A

A solution of 10 mg rizatriptan benzoate in a mixture of 1 ml 2-propanol and 0.1 ml water is evaporated in a glass vial at ambient atmosphere, yielding Form A quantitatively. The obtained crystal Form A is characterized by an X-ray powder diffraction pattern as shown in FIG. 1.

EXAMPLE 7

Preparation of Form A 13 mg rizatriptan benzoate are dissolved in 2 ml 1-butanol at 60° C. The clear solution was cooled to room temperature and seeded with 0.5 mg crystals of rizatriptan benzoate Form A.

After addition of 13 ml heptane precipitation starts. After filtration of the obtained suspension, 10 mg of Form A was obtained as a white powder. Microscopic inspection of the white powder shows that the obtained crystals are plate like particles. The obtained crystal Form A is characterized by an X-ray powder diffraction pattern as shown in FIG. 1.

EXAMPLE 8

Preparation of Form B 75 mg of rizatriptan benzoate are dissolved in 0.5 ml methanol at 60° C. The solution is added to 14 ml ethyl acetate at room temperature, and subsequently 10 ml heptane are added to the clear solution. After about 15 minutes after addition of heptane, crystallization is observed when clusters of needles start to grow. The obtained suspension is further stored at room temperature for one hour and filtered through a glass filter. 32 mg of Form B as a white solid were obtained are dried at room temperature. The obtained crystal Form B is characterized by an X-ray powder diffraction pattern as shown in FIG. 2.

EXAMPLE 9

Preparation of Form B 130 mg of rizatriptan benzoate are dissolved in 0.5 ml methanol at 60° C. The prepared solution is added to 14 ml ethyl acetate at −18° C. before seeding with 5 mg of rizatriptan benzoate Form B. After about one minute the precipitation starts. The obtained suspension is filtered, and the obtained white solid is dried in an air flow, yielding 82 mg Form B. The obtained crystal Form B is characterized by an X-ray powder diffraction pattern as shown in FIG. 2.

EXAMPLE 10

Preparation of Form B 27 mg of rizatriptan benzoate are dissolved in 7 ml 1-butanol at 50° C. This solution is filtered through a 0.22 µm Millipore filter, cooled to room temperature, and allowed to evaporate at ambient atmosphere. After evaporation of the solvent, Form B is obtained quantitatively. The obtained crystal Form B is characterized by an X-ray powder diffraction pattern as shown in FIG. 2.

EXAMPLE 11

Preparation of Form B

A solution of rizatriptan benzoate in 2-propanol (2 mg/ml) is heated to 60° C., filtered through a 0.22 µm Millipore filter and seeded 5 wt % rizatriptan benzote Form B. The solution with the seed crystals is allowed to evaporate at ambient atmosphere. After evaporation of the solvent rizatriptan benzoate Form B is obtained quantitatively. The obtained crystal Form B is characterized by an X-ray powder diffraction pattern as shown in FIG. 2.

EXAMPLE 12

Preparation of Form A 7 mg rizatriptan benzoate Form A and 7 mg Form B are suspended in 1 ml ethyl acetate, and stirred 16 hours at 25° C. After filtration, a white powder is obtained. Characterization by X-ray powder diffraction shows that rizatriptan benzoate Form A is obtained, showing that Form A is the thermodynamically most stable form and that Form B is a metastable form.

X-ray powder diffraction measurements were performed on a Philips 1710 powder X-ray diffractometer using Cu Kα radiation (Cu Kα$_1$=1.54060 Å). The X-ray source is operated at 45 kV and 45 mA. Spectra are recorded at a step size of 0.02° with a counting time of 2.4 seconds per step. The accuracy of the 2 theta values of conventionally recorded powder X-ray diffraction patterns is generally ±0.1-0.2°. For sample preparation, about 40 mg of substance was prepared into circular shaped quartz sample holders of 0.5 mm depth and 10 mm width.

The invention claimed is:

1. A crystalline polymorph Form B of N,N-dimethyl-5-(1H-1,2,4-triazol-1-ylmethyl)-1H-indole-3-ethanamine benzoate which exhibits a characteristic X-ray powder diffraction pattern with characteristic peaks expressed in d-values (Å) at 10.4 (vs), 5.45 (s), 4.95 (s), 4.71 (s); wherein (vs) stands for very strong intensity; (s) stands for strong intensity.

2. A crystalline polymorph Form B of N,N-dimethyl-5-(1H-1,2,4-triazol-1-ylmethyl)-1H-indole-3-ethanamine benzoate which exhibits a characteristic X-ray powder diffraction pattern with characteristic peaks expressed in d-values (Å) at 10.4 (vs), 5.89 (m), 5.45 (s), 5.35 (m), 4.95 (s), 4.71 (s), 4.45 (m), 4.36 (m), 3.97 (m), 3.92 (m), 3.89 (m), 3.76 (m), 3.70 (m); wherein (vs) stands for very strong intensity; (s) stands for strong intensity; (m) stands for medium intensity.

3. A crystalline polymorph Form B of N,N-dimethyl-5-(1H-1,2,4-triazol-1-ylmethyl)-1H-indole-3-ethanamine benzoate which exhibits a characteristic X-ray powder diffraction pattern with characteristic peaks expressed in d-values (Å) at 10.4 (vs), 5.89 (m), 5.45 (s), 5.35 (m), 5.18 (w), 4.95 (s), 4.71 (s), 4.45 (m), 4.36 (m), 4.23 (w), 4.18 (w), 3.97 (m), 3.92 (m), 3.89 (m), 3.76 (m), 3.70 (m), 3.50 (w), 3.45 (w), 2.72 (w); wherein (vs) stands for very strong intensity; (s) stands for strong intensity; (m) stands for medium intensity; (w) stands for weak intensity.

Figure 1:
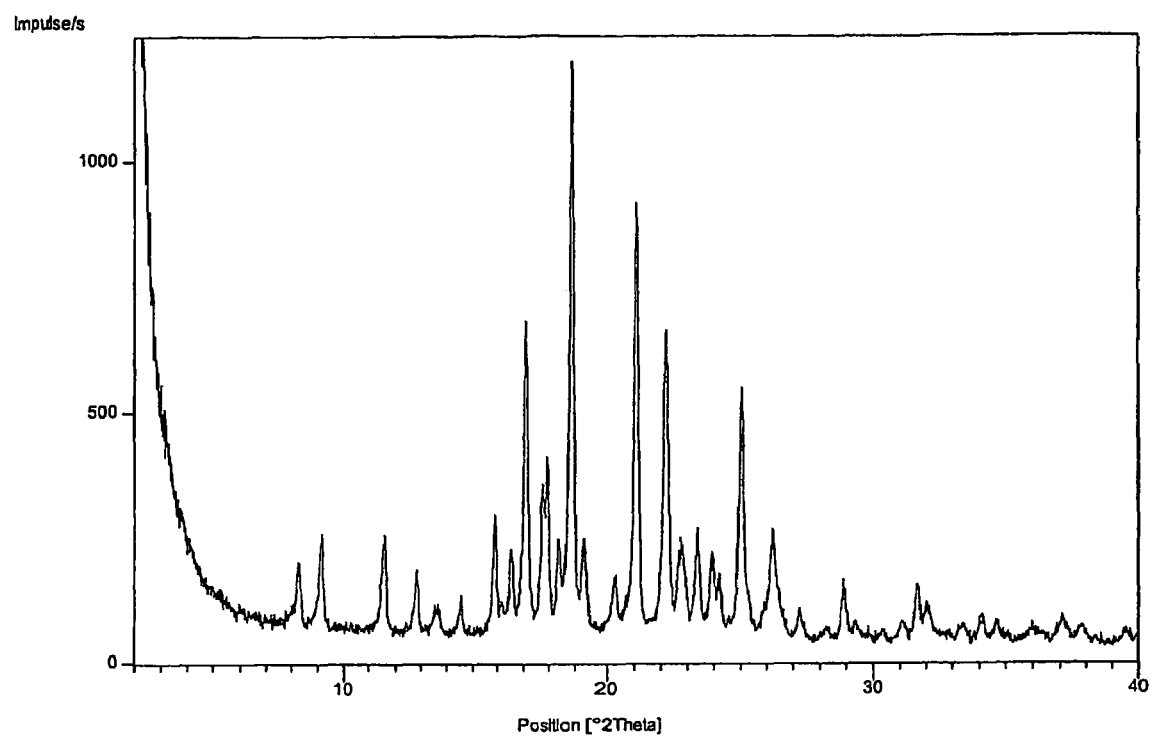
FIG. 1 is a characteristic X-ray powder diffraction pattern for Form A.
Figure 2:
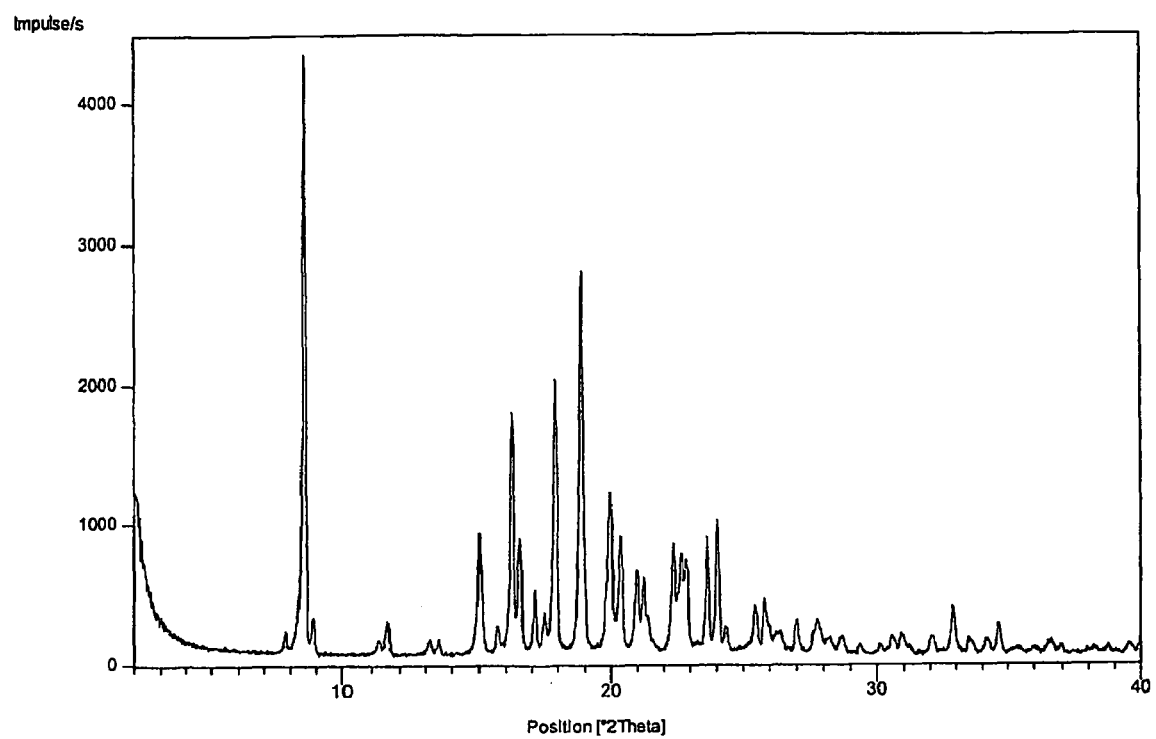
FIG. 2 is a characteristic X-ray powder diffraction pattern for Form B.

4. A crystalline polymorph Form B of N,N-dimethyl-5-(1H-1,2,4-triazol-1-ylmethyl)-1H-indole-3-ethanamine benzoate having an X-ray powder diffraction pattern substantially as depicted in FIG. 2.

5. A process for the preparation of a crystalline polymorph according to claim 1, in which a solution of Rizatriptan benzoate in an alcohol, or in a mixture of an alcoholic and another organic solvent, is added to a non-solvent.

6. A process for the preparation of a crystalline polymorph according to claim 1, in which a non-solvent is added to a solution of Rizatriptan benzoate in an alcohol or in a mixture of an alcohol with another organic solvent.

7. The process according to claim 5 in which the solution of Rizatriptan benzoate is in methanol or in a mixture of methanol and ethyl acetate.

8. The process according to claim 5 in which the non-solvent is an alkane.

9. The process according to claim 8 in which the non-solvent is hexane or heptane.

10. A process for the preparation of a crystalline polymorph according to claim 1, in which a solution of Rizatriptan benzoate in an alcohol is evaporated to dryness.

11. The process according to claim 10 in which the alcohol is 2-propanol or 1-butanol.

12. The process according to claim 11, wherein seeding is carried out with crystals of the desired crystalline polymorph.

13. The process according to claim 11, in which the solution of Rizatriptan benzoate is prepared in situ.

14. The process according to claim 13 in which the solution of Rizatriptan benzoate is prepared upon reaction of rizatriptan free base with benzoic acid.

* * * * *

UNITED STATES PATENT AND TRADEMARK OFFICE
CERTIFICATE OF CORRECTION

PATENT NO.        : 7,777,049 B2                                                                Page 1 of 1
APPLICATION NO.   : 10/585448
DATED             : August 17, 2010
INVENTOR(S)       : Paul Adriaan Van Der Schaaf et al.

It is certified that error appears in the above-identified patent and that said Letters Patent is hereby corrected as shown below:

On the Title page, please change the country of citizenship for the first inventor, Paul Adriaan Van Der Schaaf, from "FR" to --NL--, as correctly indicated on the Application Data Sheet submitted with the application on July 7, 2006, a copy of which is attached.

Signed and Sealed this

Ninth Day of November, 2010

David J. Kappos
*Director of the United States Patent and Trademark Office*